US009045777B2

(12) United States Patent
Choi et al.

(10) Patent No.: US 9,045,777 B2
(45) Date of Patent: Jun. 2, 2015

(54) POL I PROMOTER DERIVED FROM VERO CELLS AND RECOMBINANT VECTOR CONTAINING SAME

(71) Applicants: Korea Center for Disease Control and Prevention, Cheongwon-gun, Chungcheonbuk- (KR); Chungbuk National University Industry-Academic Cooperation Foundation, Cheongju, Chungcheongbuk-Do (KR)

(72) Inventors: Young Ki Choi, Chungcheongbuk-Do (KR); Chun Kang, Chungcheongnam-Do (KR); Kee Jong Hong, Seoul (KR); Min Suk Song, Chungcheongbuk-Do (KR); Yun Hee Baek, Chungcheongbuk-Do (KR)

(73) Assignees: Korea Center for Disease Control and Prevention, Cheongwon-gun, Chungcheongbuk-do (KR); Chungbuk National University Industry-Academic Cooperation Foundation, Cheongju, Chungcheongbuk-do (KR)

( * ) Notice: Subject to any disclaimer, the term of this patent is extended or adjusted under 35 U.S.C. 154(b) by 0 days.

(21) Appl. No.: 14/029,465

(22) Filed: Sep. 17, 2013

(65) Prior Publication Data

US 2014/0011260 A1 Jan. 9, 2014

Related U.S. Application Data

(63) Continuation of application No. PCT/KR2012/001919, filed on Mar. 16, 2012.

(30) Foreign Application Priority Data

Mar. 17, 2011 (KR) ........................ 10-2011-0023992

(51) Int. Cl.
*C12N 15/85* (2006.01)
*C12N 7/00* (2006.01)
*C12N 9/12* (2006.01)

(52) U.S. Cl.
CPC ...... *C12N 15/85* (2013.01); *C12N 2760/16152* (2013.01); *C12N 2760/16151* (2013.01); *C12N 2760/16051* (2013.01); *C12N 7/00* (2013.01); *C12N 2830/85* (2013.01); *C12N 9/1252* (2013.01); *C12Y 207/07007* (2013.01); *C12N 2760/16052* (2013.01)

(58) Field of Classification Search
CPC .................... C12N 15/63; C12N 2760/18534; C12N 2320/32; C12N 2830/008; C12N 2830/007; C12N 2760/16051; C12N 2760/16052; C12N 2760/16151; A61K 39/145; A61K 39/12; C07K 14/005; C07K 16/1018; C07K 2317/14
See application file for complete search history.

(56) References Cited

U.S. PATENT DOCUMENTS

| 2004/0029251 A1* | 2/2004 | Hoffman et al. ............. 435/239 |
| 2007/0134270 A1* | 6/2007 | Naffakh et al. ............ 424/209.1 |
| 2012/0189656 A1* | 7/2012 | Dormitzer et al. ......... 424/204.1 |

FOREIGN PATENT DOCUMENTS

WO 2011/012999 A1 2/2011

OTHER PUBLICATIONS

Song MS, Baek YH, Pascua PN, Kwon HI, Park SJ, Kim EH, Lim GJ, Choi YK. Establishment of Vero cell RNA polymerase I-driven reverse genetics for Influenza A virus and its application for pandemic (H1N1) 2009 influenza virus vaccine production. J Gen Virol. Jun. 2013;94(Pt 6):1230-5. Epub Mar. 13, 2013.*
Massin, P. et al. "Cloning of the Chicken RNA Polymerase I Promoter and Use for Reverse Genetics of Influenza A Viruses in Avian Cells", Journal of Virology, vol. 79(21), pp. 13811-13816 (Nov. 2005).
Murakami, S. et al. "Establishment of Canine RNA Polymerase I-Driven Reverse Genetics for Influenza A Virus: Its Application for H5N1 Vaccine Production", Journal of Virology, vol. 82(3), pp. 1605-1609 (Nov. 28, 2007).
Palmer, T.D. et al. "Efficient expression of a protein coding gene under the control of an RNA polymerase I promoter", Nucleic Acids Research, vol. 21(15), pp. 3451-3457 (Jul. 25, 1993).
Suphaphiphat, P. et al., "Human RNA Polymerase I-Driven Reverse Genetics for Influenza A Virus in Canine Cells", Journal of Virology, vol. 84(7), pp. 3721-3725 (Jan. 13, 2010).
Wang, Z. et al. "Cloning of the canine RNA polymerase I promoter and establishment of reverse genetics for influenza A and B in MDCK cells", Virology Journal, vol. 4:102 (2007).
Extended European Search Report for European Application No. 12757721.1, dated Apr. 8, 2015, 9 pages.
Song, M.S. et al, "Establishment of Vero cell RNA polymerase I-driven reverse genetics for Influenza a virus and its application for pandemic (H1N1) 2009 influenza virus vaccine production", Jrl. Gen. Virology (2013) 94, pp. 1230-1235.

(Continued)

*Primary Examiner* — Benjamin P Blumel
*Assistant Examiner* — Rachel Gill
(74) *Attorney, Agent, or Firm* — Mintz Levin Cohn Ferris Glovsky and Popeo, P.C.; Kongsik Kim

(57) ABSTRACT

The present invention relates to a pol I promoter derived from Vero cells and a recombinant vector containing the same. When the pol I promoter derived from Vero cells according to the present invention is utilized, viruses can be manufactured efficiently, and consequently, the manufacture of both seasonal influenza vaccine and pandemic vaccine can be prepared more quickly to usefully address either situation.

8 Claims, 6 Drawing Sheets

(56) References Cited

OTHER PUBLICATIONS

Neumann, G. et al., "Generation of influenza A viruses entirely from cloned cDNAs", Proc. Natl. Acad. Sci. USA, vol. 96, pp. 9345-9350 (Aug. 1999).

Ozaki, H. et al, "Generation of High-Yielding Influenza A Viruses in African Green Monkey Kidney (Vero) Cells by Reverse Genetics", Journal of Virology, vol. 78, No. 4, pp. 1851-1857 (Feb. 2004).

* cited by examiner

ID NO:2.

POL I PROMOTER DERIVED FROM VERO CELLS AND RECOMBINANT VECTOR CONTAINING SAME

CROSS-REFERENCE TO RELATED APPLICATIONS

This is a continuation of International Application No. PCT/KR2012/001919 filed on Mar. 16, 2012, which claims priority to Korean Application No. 10-2011-0023992 filed on Mar. 17, 2011, which applications are incorporated herein by reference.

TECHNICAL FIELD

The present invention relates to a pol I promoter derived from Vero cells and a recombinant vector comprising the same.

BACKGROUND ART

Since human infection by avian influenza occurred in Hong Kong in 1997, outbreaks have been recently increasing in China and Southeast Asian countries such as Vietnam and Indonesia. Besides, at the time of co-infection with both human influenza and avian influenza, there has been high possibility of emergence of influenza virus variants which may infect people due to gene shift between the two influenza viruses (Chen et al., 2008). In recent years, it has been reported all over the world that the new H1N1 influenza virus derived from swine viruses infected and killed people, and the World Health Organization (WHO) also has warned of the outbreak of a new type of epidemic influenza virus and recommended each country to establish countermeasures against this possibility (WHO, 2009; Garten et al., 2009; Smith et al., 2009). There is still no effective preventive vaccine worldwide. Tamiflu, as the treatment that is currently in use, is in short supply and is produced at an enormous cost. Moreover, Tamiflu resistant viruses have been recently discovered, with the result that, when a new influenza pandemic arises, the technology for treating it is absent in the world.

In the present, reverse genetic pol I-pol II promoter systems used all around the world employ a human-derived promoter (Hoffmann et al., 2000). The thus developed human promoter systems are effectively operated in 293T cells, which are human-derived cell lines, to effectively create viruses, but the recombinant virus to be used for producing human vaccines cannot use cancer cells from human. Therefore, the Food and Drug Administration (FDA) in USA and the WHO have recommended Vero cells derived from African green monkeys (WHO, 2005). Although the human-derived pol I and pol II promoters operate the Vero cells derived from monkeys to some degree, the virus recovery rate is low as compared with for human-derived cells. Due to this low recovery rate, France tried to use chicken-derived pol I and pol II promoters to increase the virus recovery rate. Dr. Kawaoka's group in the USA succeeded in finding promoters derived from Madin-Darby Canine Kidney (MDCK) cells, and thus obtained research results of increasing the virus recovery rate (Massin et al., 2005; Murakami et al., 2008).

Hence, the present inventors endeavored to provide a reverse genetic method of increasing the recombinant virus recovery rate by using the pol I promoter derived from Vero cells, and as the result, they found the pol I promoter derived from Vero cells and confirmed that the virus recovery rate can be increased by using the vector comprising the Vero pol I promoter, and then completed the present invention.

SUMMARY

Therefore, the present invention has been made in view of the above-mentioned problems, and an aspect of the present invention is to provide a pol I promoter derived from Vero cells and a recombinant vector comprising the same.

In accordance with an aspect of the present invention, there is provided a promoter having a nucleotide sequence as set forth in SEQ ID NO:1 or SEQ ID NO:2.

In accordance with another aspect of the present invention, there is provided a recombinant vector for producing viruses, the recombinant vector comprising the promoter having a nucleotide sequence as set forth in SEQ ID NO:1 or SEQ ID NO:2.

In accordance with another aspect of the present invention, there is provided a Vero cell transformed with the recombinant vector.

In accordance with another aspect of the present invention, there is provided a method for producing viruses by incubating Vero cells transformed with the recombinant vector comprising the promoter having a nucleotide sequence as set forth in SEQ ID NO:1 or SEQ ID NO:2.

The promoter may be a pol I promoter derived from Vero cells.

The recombinant vector may further include one or more genes selected from the group consisting of PB2, PB1, PA, HA, NP, NA, M, and NS.

In the present invention, it was confirmed that, as pol I promoter regions derived from Vero cells, there are a promoter (SEQ ID NO: 1) having 326 nucleotides and a promoter (SEQ ID NO: 2) having 212 nucleotides, upstream from the transcription initiation site (+1).

In the present invention, the v2pHW recombinant vector was constructed by PCR-amplifying a region corresponding to the obtained pol I promoter derived from Vero cells, removing the human pol I promoter from the existing pHW2000 vector (empty vector of the existing reverse genetic system), and then substituting the pol I promoter-guessable region derived from Vero cells therefor. Then, eight genes of the PR/8/34 virus was inserted into the recombinant vector, and it was confirmed whether or not the pol I promoter derived from Vero cells is effectively operated.

In the present invention, in order to check the protein expression efficiency of the recombinant vector comprising the pol I promoter derived from Vero cells, the existing pHW72-GFP vector developed by Hoffmann was modified to manufacture the v2pHW-GFP/luciferase vector prior to measurement.

As set forth above, when the pol I promoter derived from Vero cells according to the present invention is used, the viruses can be efficiently produced, thereby quickly producing pandemic vaccines as well as seasonal influenza vaccines, and thus, the present invention is useful.

BRIEF DESCRIPTION OF THE DRAWINGS

FIG. 1A is a diagram showing a promoter region prior to the 18S gene of each repeat unit, and FIG. 1B is a comparative diagram of −8th to +11th nucleotide based on the transcription initiation site (+1) among Vero cells, human cells, and others;

DETAILED DESCRIPTION

Hereinafter, the present invention will be described in detail with reference to the following examples. However, the following examples are merely for illustrating the present invention and are not intended to limit the scope of the present invention.

Example 1

Searching of Promoter Gene Derived from Vero Cells

Vero cells were treated with RNase to extract purely separated genomic DNA, and then various primers were prepared based on the nucleotide sequence of the 18S gene derived from human cells. Then, various combinations of PCR thereof were conducted and similar sizes of PCR products were purified, which were then cloned into the TA vectors (Promega), and then clones showing an insert having the same size as the PCR product were subjected to gene analysis.

Figure 1:
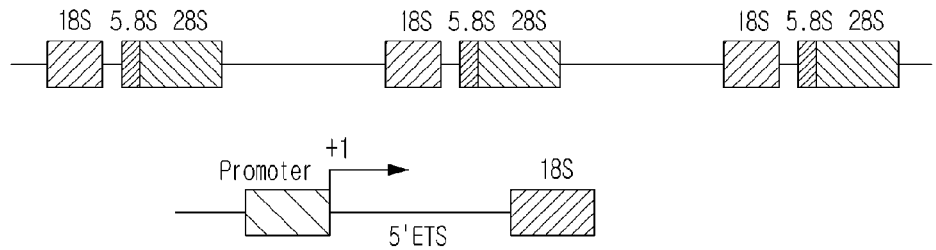
FIG. 1 simply illustrates ribosomal RNA transcription regions repeated in a mammal, and specifically.
Figure 2:
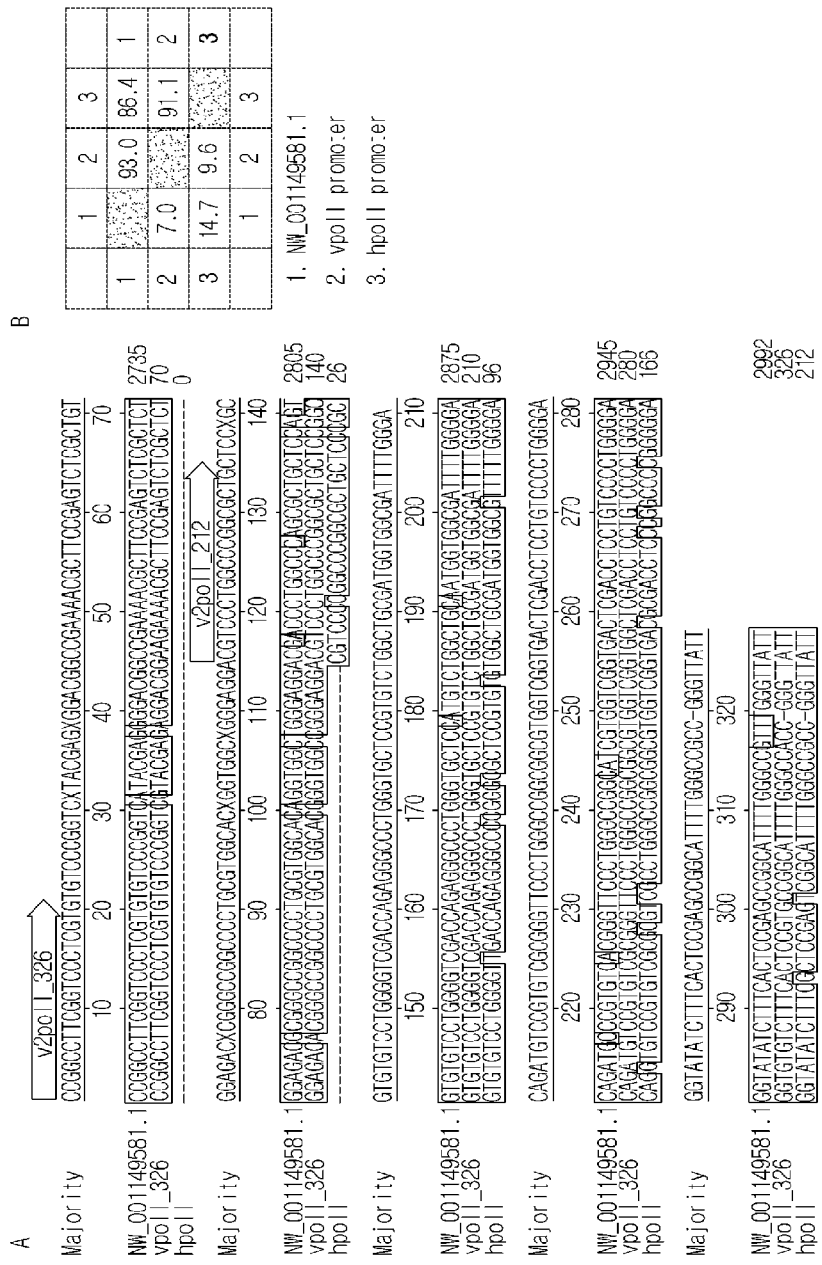
FIG. 2 compares the nucleotide sequence among the Vero pol I promoter (326), and *Macaca mulatta* pol I promoter (NW_001149581.1) and human pol I promoter, which are registered in GenBank.
Figure 3:
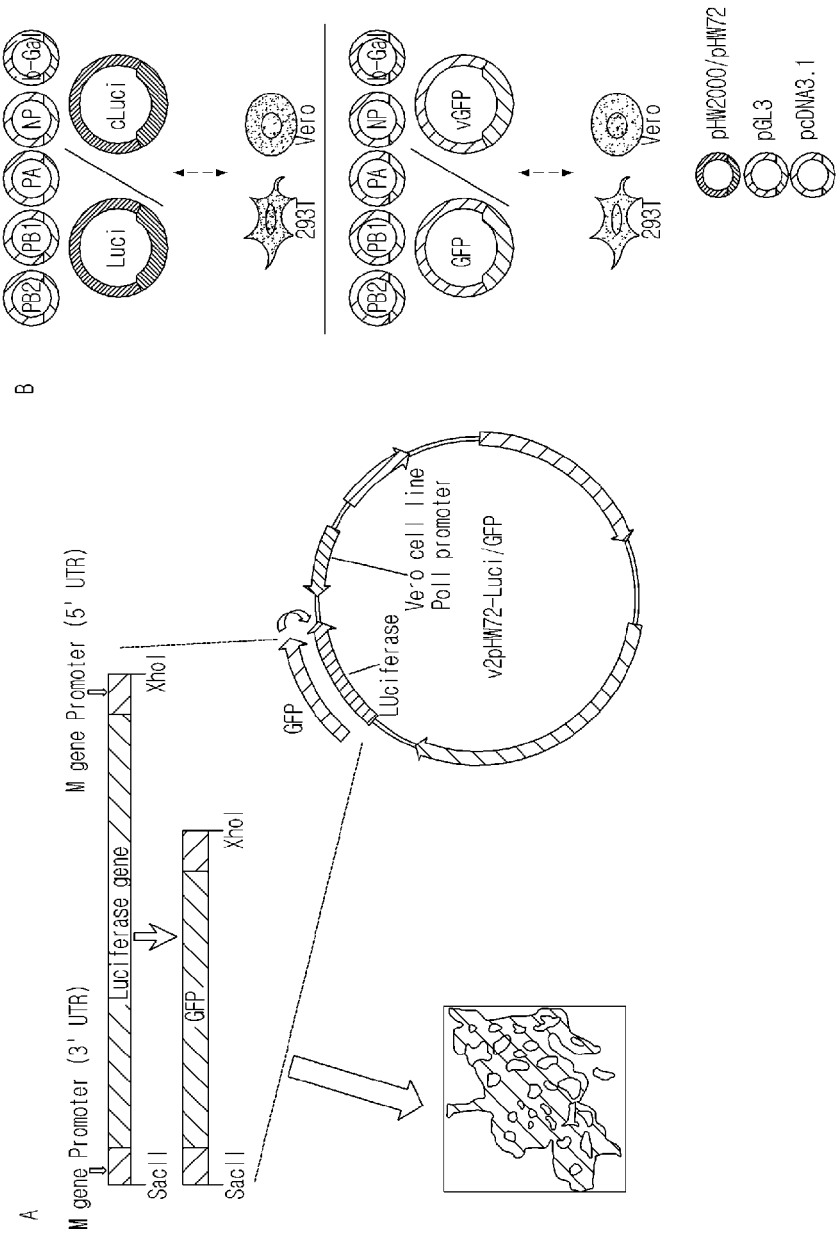
FIG. 3A is a diagram illustrating that the v2pHW72-luci/GFP vector is established by substituting the human pol I promoter with the Vero pol I promoter in the existing pHW72-luci/GFP vector.
FIG. 3B is a diagram illustrating that PB2, PB1,PA, and NP genes of the PR/8/34 virus are cloned into the pcDNA3.1 myc-His(+) vectors and then the v2pHW72-luci/GFP vector is used to measure luciferase and GFP activities by the promoter in the 293T cells and the Vero cells.

In the present invention, the Vero pol I promoter region was expected by comparing the nucleotide sequence between the analyzed genes and human pol I promoter (GenBank accession no. U13369.1), or comparing the nucleotide sequences of the analyzed genes with the non-human primate *Macaca mulatta* whole genome shotgun sequence (GenBank accession no. NW_001149581.1) and the *Macaca mulatta* chromosome 20 genomic scaffold, whole genome shotgun sequence (GenBank accession no. NW_001111333.1) obtained through the blast search in GenBank. As a result of analyzing the Vero pol I promoter region based on this, 326 nucleotides in total upstream from the transcription initiation site was confirmed, as shown in FIG. 2. This showed to have about 91.1% homology to the human pol I promoter, and about 93% homology to the *Macaca mulatta* pol I promoter (NW_001149581.1), which is somewhat higher than that of the human pol I promoter.

Example 2

Construction of Vero Pol I Promoter Vector System

The human pol I promoter region was removed by using KpnI, which is a restriction enzyme region in the pHW2000 vector (St. Jude Children's Research Hospital), and newly prepared BamHI, and then the Vero pol I promoter-guessable region, of which the gene nucleotide sequence was confirmed through PCR amplification, was inserted thereinto, which is then called the vpHW vector.

Then, influenza virus universal primers proposed by Hoffmann were used to amplify eight genes (PB2, PB1, PA, HA, NP, NA, M, and NS) of the PR/8/34 virus, which is a backbone for producing influenza virus vaccines, by a reverse genetic method, and then the amplified genes were inserted into the newly modified vpHW vector. The inserted genes were analyzed to check whether or not the same virus genes were inserted.

The primers used are as follows.

TABLE 1

| Primer | Sequence |
|---|---|
| Bm HA-1F | TATTCGTCTCAGGGAGCAAAAGCAGGGG (SEQ ID NO: 3) |
| Bm NS-1F | TATTCGTCTCAGGGAGCAAAAGCAGGGTG (SEQ ID NO: 4) |
| Bm NS-890-R | ATATCGTCTCGTATTAGTAGAAACAAGGGTGTTTT (SEQ ID NO: 5) |
| Ba NA-1F | TATTGGTCTCAGGGAGCAAAAGCAGGAGT (SEQ ID NO: 6) |
| Ba NA-1413R | ATATGGTCTCGTATTAGTAGAAACAAGGAGTTTTTT (SEQ ID NO: 7) |
| Bm M-1F | TATTCGTCTCAGGGAGCAAAAGCAGGTAG (SEQ ID NO: 8) |
| Bm M-1027R | ATATCGTCTCGTATTAGTAGAAACAAGGTAGTTTTT (SEQ ID NO: 9) |
| Bm NP-1F | TATTCGTCTCAGGGAGCAAAAGCAGGGTA (SEQ ID NO: 10) |
| Bm NP-1565R | ATATCGTCTCGTATTAGTAGAAACAAGGGTATTTTT (SEQ ID NO: 11) |
| Bm PA-1F | TATTCGTCTCAGGGAGCGAAAGCAGGTAC (SEQ ID NO: 12) |
| Bm PA-2233R | ATATCGTCTCGTATTAGTAGAAACAAGGTACTT (SEQ ID NO: 13) |
| Bm PB1-1F | TATTCGTCTCAGGGAGCGAAAGCAGGCA (SEQ ID NO: 14) |
| Bm PB1-2341R | ATATCGTCTCGTATTAGTAGAAACAAGGCATTT (SEQ ID NO: 15) |
| Ba PB2-1F | TATTGGTCTCAGGGAGCGAAAGCAGGTC (SEQ ID NO: 16) |
| Ba PB2-2341R | ATATGGTCTCGTATTAGTAGAAACAAGGTCGTTT (SEQ ID NO: 17) |

Example 3

Virus Production Efficiency Using Vero Pol I Promoter System

Figure 6:
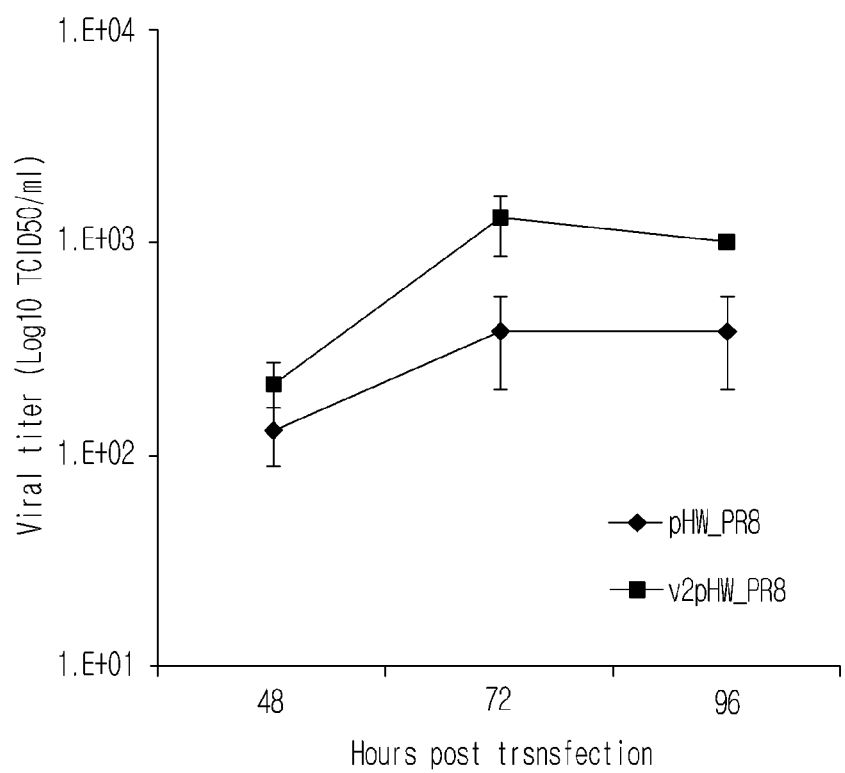
FIG. 6 shows virus production efficiency between the existing human pol I promoter system and the Vero pol I promoter system in the MDCK cells by the time-specific virus titer TCID50/ml post transfection.

Eight genes, which are to be used in a PR/8/34 virus reverse genetic system containing the existing human pol I promoter and a PR/8/34 virus reverse genetic system containing the newly modified Vero pol I promoter, were identically prepared. After that, three sets of eight genes were prepared for each group having the same amount of Vero cells, followed by transfection under the same conditions, and then the amounts of viruses produced for 48, 72, and 96 hours were measured in MDCK (madin-darby canine kidney) cells by the 50% Tissue Culture Infective Dose (TCID50/ml). As the result, it was confirmed that the titer (TCID50/ml) of the PR/8/34 virus produced by the Vero pol I promoter developed by the present invention was about 3 to 4 fold higher than that of the existing system on 72 hours post transfection, which showed higher virus production efficiency (FIG. 6).

Example 4

Efficiency of Vero Pol I Promoter Through Measurements of Luciferase and GFP Activities The efficiency of the promoter in the Vero cells and 293T cells can be determined by measuring luciferase and Green Fluorescent Protein (GFP) activities under the polymerases of the same virus. Therefore, PB2, PB1, PA, and NP genes of the PR/8/34 virus were cloned into the pcDNA3.1 myc-His (+) vectors, and then the Vero cells and the 293T cells were simultaneously transfected with the v2pHW72-Luciferase/GFP vector in which the four vectors and the Vero pol I promoter were inserted. After 24 to 36 hours, the trasnsfected cells were collected, followed by measurement of luciferase and GFP activities.

Figure 4:
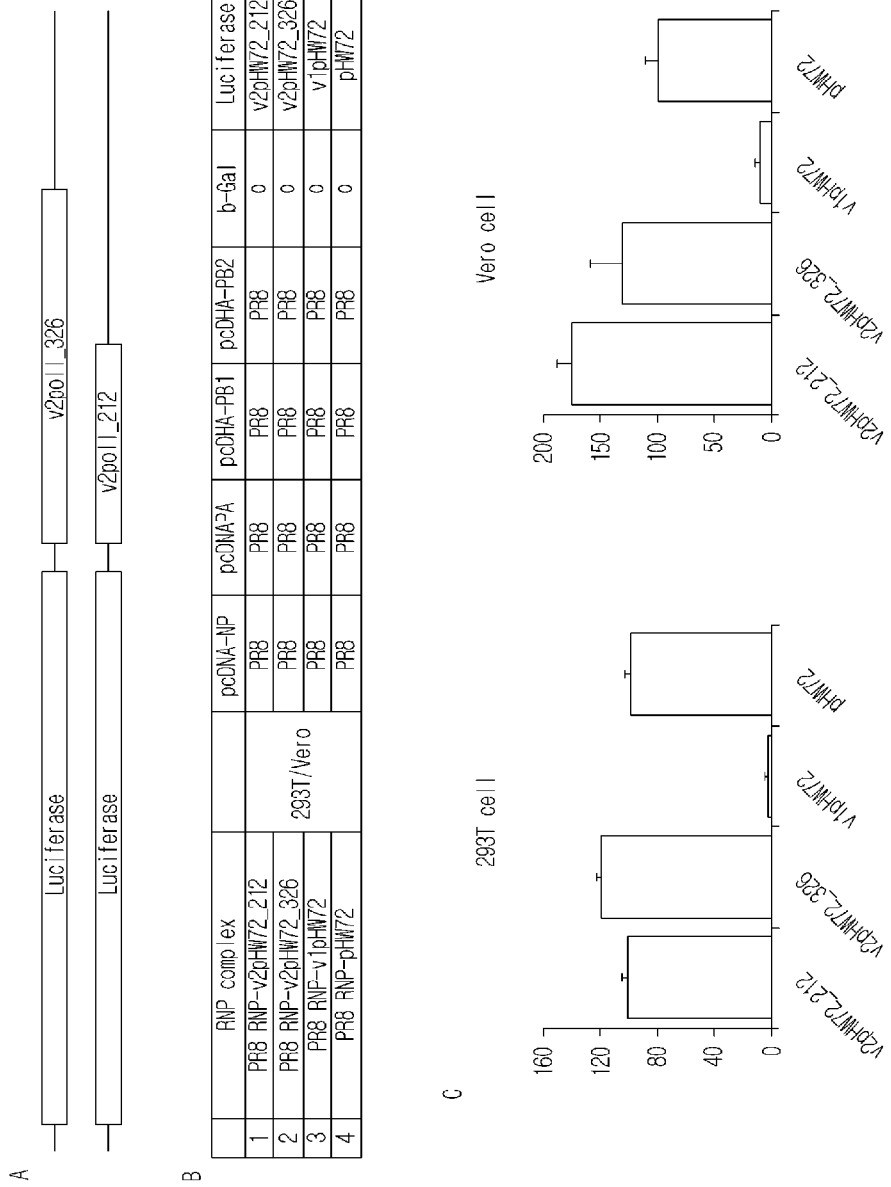
FIG. 4 compares luciferase activities for the human pol I promoter and the Vero pol 1 promoter, which were measured in the 293T cells and Vero cells.
Figure 5:
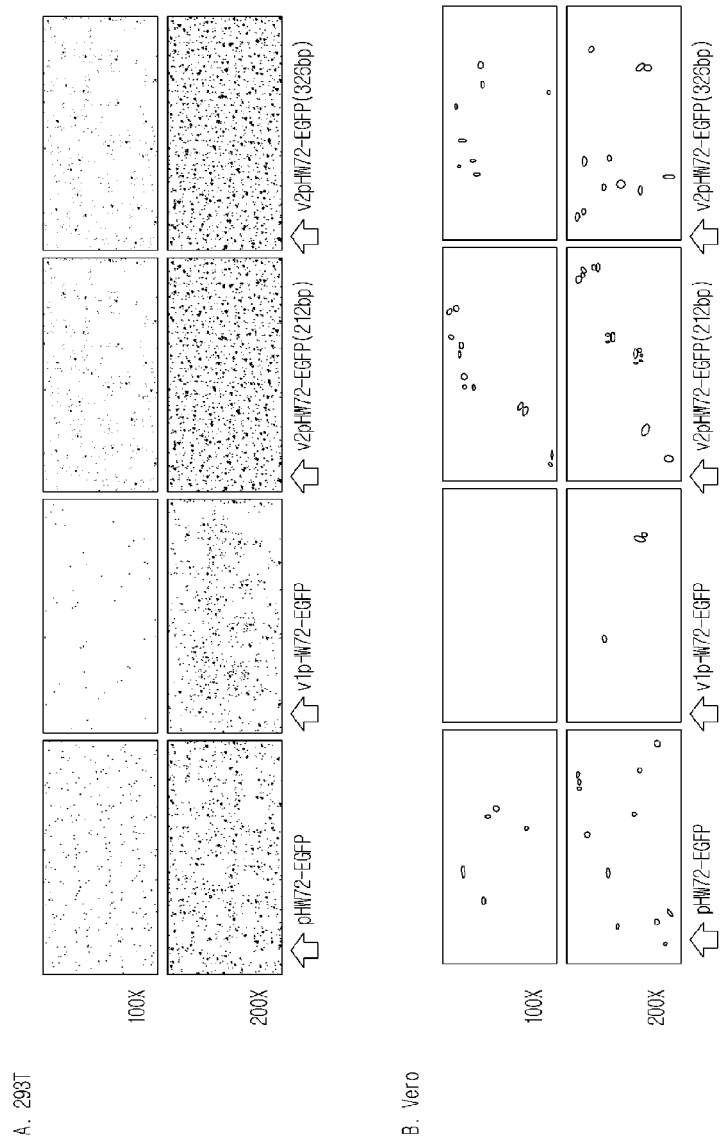
FIG. 5 compares GFP activities for the human pol I promoter and the Vero pol 1 promoter, which were measured in the 293T cells and Vero cells.

As the result, as shown in FIGS. 4 and 5, the luciferase activity in the 293T cells did not show a large difference among 212 and 326 nucleotide-sized Vero pol I promoters (v2pHW72_212 and v2pHW72-326) and the human pol I promoter (pHW72), but the luciferase activity in the Vero cells exhibited 1.7 to 2 fold higher for the Vero pol I promoters than the human pol I promoter. These results confirmed that the use of the pol I promoter derived from the Vero cells can lead to higher virus production efficiency than the existing human pol I promoter.

The invention claimed is:

1. An RNA polymerase I (pol I) promoter comprising a nucleotide sequence as set forth in SEQ ID NO: 1.

2. A pol I promoter comprising a nucleotide sequence as set forth in SEQ ID NO: 2.

3. A recombinant vector, wherein the recombinant vector comprises the promoter of claim 1 or 2.

4. The recombinant vector of claim 3, further comprising one or more influenza genes under the control of said promoter, wherein the influenza genes are selected from the group consisting of: PB2, PB1, PA, HA, NP, NA, M, and NS.

5. A Vero cell transfected with the recombinant vector of claim 3.

6. A method for producing influenza viruses, wherein said method comprises:
   (1) culturing Vero cells transfected with one or more recombinant vector(s), wherein said vector comprises the promoter of claim 1 operably linked to one or more influenza genes selected from the group consisting of: PB2, PB1, PA, HA, NP, NA, M, and NS; and
   (2) recovering influenza virions from the cell culture.

7. A method for producing influenza viruses, wherein said method comprises:
   (1) culturing Vero cells transfected with one or more recombinant vector(s), wherein said vector comprises the promoter of claim 2 operably linked to one or more influenza genes selected from the group consisting of: PB2, PB1, PA, HA, NP, NA, M, and NS; and
   (2) recovering influenza virions from the cell culture.

8. A Vero cell transfected with the recombinant vector of claim 4.

* * * * *

```
                         SEQUENCE LISTING

<160> NUMBER OF SEQ ID NOS: 17

<210> SEQ ID NO 1
<211> LENGTH: 326
<212> TYPE: DNA
<213> ORGANISM: Chlorocebus sp.

<400> SEQUENCE: 1
ccggccttcg gtccctcgtg tgtcccggtc gtacgagagg acggccgaaa acgcttccga      60
gtctcgctct ggagacacgg gccggcccct gcgtggcacg ggtggccggg aggacgtccc     120
tggcccggcg ctgctccggc gtgtgtcctg gggtcgacca gagggccctg ggtgctccgt     180
gtctggctgc gatggtggcg attttgggga cagatgtccg tgtcgcgggt tccctgggcc     240
ggcggcgtgg tcggtggctc gacctcctgt ccctgggga ggtatatctt tcactccgag     300
ccggcatttt gggccaccgg gttatt                                          326

<210> SEQ ID NO 2
<211> LENGTH: 212
<212> TYPE: DNA
<213> ORGANISM: Chlorocebus sp.

<400> SEQUENCE: 2
cgtccctggc ccggcgctgc tccggcgtgt gtcctggggt cgaccagagg gccctgggtg      60
ctccgtgtct ggctgcgatg gtggcgattt tggggacaga tgtccgtgtc gcgggttccc     120
tgggccggcg gcgtggtcgg tggctcgacc tcctgtcccc tggggaggta tatctttcac     180
tccgagccgg cattttgggc caccgggtta tt                                   212

<210> SEQ ID NO 3
<211> LENGTH: 28
<212> TYPE: DNA
<213> ORGANISM: Artificial Sequence
<220> FEATURE:
<223> OTHER INFORMATION: primer

<400> SEQUENCE: 3
tattcgtctc agggagcaaa agcagggg                                        28

<210> SEQ ID NO 4
<211> LENGTH: 29
<212> TYPE: DNA
<213> ORGANISM: Artificial Sequence
<220> FEATURE:
```

```
<223> OTHER INFORMATION: primer

<400> SEQUENCE: 4
tattcgtctc agggagcaaa agcagggtg                                    29

<210> SEQ ID NO 5
<211> LENGTH: 35
<212> TYPE: DNA
<213> ORGANISM: Artificial Sequence
<220> FEATURE:
<223> OTHER INFORMATION: primer

<400> SEQUENCE: 5
atatcgtctc gtattagtag aaacaagggt gtttt                             35

<210> SEQ ID NO 6
<211> LENGTH: 29
<212> TYPE: DNA
<213> ORGANISM: Artificial Sequence
<220> FEATURE:
<223> OTHER INFORMATION: primer

<400> SEQUENCE: 6
tattggtctc agggagcaaa agcaggagt                                    29

<210> SEQ ID NO 7
<211> LENGTH: 36
<212> TYPE: DNA
<213> ORGANISM: Artificial Sequence
<220> FEATURE:
<223> OTHER INFORMATION: primer

<400> SEQUENCE: 7
atatggtctc gtattagtag aaacaaggag tttttt                            36

<210> SEQ ID NO 8
<211> LENGTH: 29
<212> TYPE: DNA
<213> ORGANISM: Artificial Sequence
<220> FEATURE:
<223> OTHER INFORMATION: primer

<400> SEQUENCE: 8
tattcgtctc agggagcaaa agcaggtag                                    29

<210> SEQ ID NO 9
<211> LENGTH: 36
<212> TYPE: DNA
<213> ORGANISM: Artificial Sequence
<220> FEATURE:
<223> OTHER INFORMATION: primer

<400> SEQUENCE: 9
atatcgtctc gtattagtag aaacaaggta gtttt                             36

<210> SEQ ID NO 10
<211> LENGTH: 29
<212> TYPE: DNA
<213> ORGANISM: Artificial Sequence
<220> FEATURE:
<223> OTHER INFORMATION: primer

<400> SEQUENCE: 10
tattcgtctc agggagcaaa agcagggta                                    29
```

```
<210> SEQ ID NO 11
<211> LENGTH: 36
<212> TYPE: DNA
<213> ORGANISM: Artificial Sequence
<220> FEATURE:
<223> OTHER INFORMATION: primer

<400> SEQUENCE: 11
atatcgtctc gtattagtag aaacaagggt attttt                                36

<210> SEQ ID NO 12
<211> LENGTH: 29
<212> TYPE: DNA
<213> ORGANISM: Artificial Sequence
<220> FEATURE:
<223> OTHER INFORMATION: primer

<400> SEQUENCE: 12
tattcgtctc agggagcgaa agcaggtac                                        29

<210> SEQ ID NO 13
<211> LENGTH: 33
<212> TYPE: DNA
<213> ORGANISM: Artificial Sequence
<220> FEATURE:
<223> OTHER INFORMATION: primer

<400> SEQUENCE: 13
atatcgtctc gtattagtag aaacaaggta ctt                                   33

<210> SEQ ID NO 14
<211> LENGTH: 28
<212> TYPE: DNA
<213> ORGANISM: Artificial Sequence
<220> FEATURE:
<223> OTHER INFORMATION: primer

<400> SEQUENCE: 14
tattcgtctc agggagcgaa agcaggca                                         28

<210> SEQ ID NO 15
<211> LENGTH: 33
<212> TYPE: DNA
<213> ORGANISM: Artificial Sequence
<220> FEATURE:
<223> OTHER INFORMATION: primer

<400> SEQUENCE: 15
atatcgtctc gtattagtag aaacaaggca ttt                                   33

<210> SEQ ID NO 16
<211> LENGTH: 28
<212> TYPE: DNA
<213> ORGANISM: Artificial Sequence
<220> FEATURE:
<223> OTHER INFORMATION: primer

<400> SEQUENCE: 16
tattggtctc agggagcgaa agcaggtc                                         28

<210> SEQ ID NO 17
<211> LENGTH: 34
<212> TYPE: DNA
<213> ORGANISM: Artificial Sequence
<220> FEATURE:
<223> OTHER INFORMATION: primer
```

-continued

```
<400> SEQUENCE: 17
atatggtctc gtattagtag aaacaaggtc gttt                                34
```